United States Patent [19]

Etheredge, III et al.

[11] Patent Number: 4,938,746
[45] Date of Patent: Jul. 3, 1990

[54] NOVEL NASOGASTRIC DEVICE

[75] Inventors: Robert W. Etheredge, III, Natick; John C. Charkoudian, Newton, both of Mass.

[73] Assignee: The Kendall Company, Boston, Mass.

[21] Appl. No.: 173,340

[22] Filed: Mar. 25, 1988

[51] Int. Cl.⁵ .......................................... A61M 25/00
[52] U.S. Cl. ..................................... 604/265; 604/270
[58] Field of Search ................. 604/95, 170, 264, 265, 604/270

[56] References Cited

U.S. PATENT DOCUMENTS

| | | | |
|---|---|---|---|
| 4,206,060 | 6/1980 | Yamamoto et al. | 411/373 X |
| 4,257,421 | 3/1981 | Beal | 604/265 X |
| 4,589,873 | 5/1986 | Schwartz et al. | 604/265 |
| 4,670,248 | 6/1987 | Schricher | 424/155 X |

Primary Examiner—Dalton L. Truluck

[57] ABSTRACT

Nasogastric intubation device having a removable stylet or stiffening wire to facilitate proper intubation, wherein the stylet is provided with a surface coating consisting essentially of alkaline earth metal salts of an unsaturated and a saturated higher fatty acid containing at least 16 carbon atoms.

10 Claims, 1 Drawing Sheet

NASOGASTRIC DEVICE

BACKGROUND OF THE INVENTION

This invention relates to improvements in nasogastric intubation devices adapted for feeding and/or removal of fluids from the stomach. As is well known, nasogastric devices are commonly employed in postoperative abdominal surgery for emptying the stomach of secretions and gas in order to prevent gastric dilation. They are also used for attaining adequate nutrition, e.g. feeding of high protein liquids, for patients unable to take oral nourishment. Nasogastric intubation may be prescribed, for example, when the normal digestive mechanism is impaired. Impairment may range from localized trauma to the digestive tract to loss for automic function, a common side effect for stroke victims.

Whether intubation be for aspiration or removal of fluids from the stomach or for feeding, intubation is accomplished by inserting the nasogastric tube into a nostril and directing it through the esophagus to the stomach and/or small intestine if the stomach is disfunctional.

In directing the tube, anatomical angulations as well as critical bifurcations of the pathway mandate a semi-rigid object. Misguiding a nasogastric tube into the trachea rather than the esophagus, at the orophagngeal bifurcation can result in respiratory impairment, e.g. pneumothorax or puncturing of the lung. Consequently, some degree of rigidity is needed for proper guidance during intubation.

Paradoxically, however, a rigid intubation device can produce a different category of injuries, namely soft tissue injuries to the delicate mucosal lining as well as to the sinuses, epiglottis, uvula, larynx, etc. Direct impact or friction caused during intubation or removal may cause abrasions and/or hemorrhaging. Laryngitis and difficulty in swallowing are among the most frequently reported post-intubation complications, illustrating the inadequacy of the devices presently used.

It will therefore be seen that a nasogastric tube should be flexible to minimize impact and friction. On the other hand, accurate and safe guidance necessitates a rigid object, which rigidity can cause injury to soft tissues. While the prior art has addressed this paradox, it has not done so successfully.

Generally speaking, two nasogastric intubation procedures are presently dominant. The first method, which seeks to obviate the aforementioned paradox, but is less common, utilizes a flexible tube which is swallowed. This method relies upon a viable and functional swallowing mechanism, impairment of which is a reason for prescribing intubation in the first place. Accordingly, this technique has limited applicability.

The second and generally accepted procedure employs a stylet or wire guide to facilitate intubation. In this form of nasogastric intubation, the stylet is initially housed in the tube and is removed once proper positioning is obtained.

The present invention is directed to the latter device employing a stylet or stiffening wire guide to facilitate proper intubation, and, more particularly, to a novel coating for the stylet to facilitate removal without dislodgment or movement of the tube.

As will be appreciated, a nasogastric tube follows a rather tortuous path from insertion in the nasal passage and then down through the esophagus and eventually into the stomach. Because of the various angulations and the frictional forces resulting therefrom when the stylet contacts the inner wall of the tube during removal, soft tissue injuries will frequently occur.

The prior art has attempted to address this problem by proposing various coatings and/or lubricants to decrease friction and thereby lessen the danger of injury. However, none has been entirely satisfactory.

While not intending to be an exhaustive survey of the prior literature pertaining thereto, the following patents are nevertheless considered to be fairly illustrative of the state of the art pertaining to tubes having guide wires intended to be removed once the tube is in place.

U.S.P 4,257,921 of Beal proposes the use of Teflon coated wires.

U.S. Pat. No. 4,534,363 issued to Gold teaches using copolymers of methyl siloxane and amino alkyl siloxane.

U.S. Pat. No. 4,589,873 of Schwartz discloses hydrophilic polymers and PVC tubing coated with PVP, polyethylene oxide, polyhydroxyethyl methacrylate, copolymers of PVP with vinyl sulfonic acid or other vinyl acids.

U.S. Pat. No. 4,664,657 of Willamitis teaches using polydimethyl siloxane.

U.S. Pat. No. 4,666,437 of Lambert discloses applying to an article made of vinyl polymers, polyesters or polyacrylates and rubber, a solution of an isocyanate monomer having at least two unreacted isocyanate groups per molecule, an isocyanate prepolymer, or a mixture thereof.

U.S. Pat. No. 4,668,224 issued to Lentz teaches the use of a cellulose powder, e.g. acid cellulose.

Finally, British Specification No.1,600,963 teaches using an interpolymer of PVP and polyurethane.

As previously mentioned, none of the coatings or lubricants heretofore suggested have been entirely satisfactory for use with nasogastric tubes.

Accordingly, the task of this invention, simply stated, is to provide lubricious coatings for stylets utilized for intubation, which coatings employ readily available and relatively inexpensive materials to provide the requisite lubriciousness for easy removal from the tube.

BRIEF DESCRIPTION OF THE INVENTION

In accordance with the present invention, this task is solved by utilizing as the lubricating coating for the stylet a substantially homogeneous non-aqueous mixture consisting essentially of:

(1) an alkaline earth metal salt of an unsaturated higher fatty acid having at least 16 carbon atoms; and (2) up to equal parts by weight of an alkaline earth metal salt of a saturated fatty acid having at least 16 carbon atoms.

Upon applying an aqueous medium, e.g. by flushing the stylet-containing nasogastric tube with water, a lubricious coating is provided on the stylet which materially enhances removal of the stylet following intubation along with a concomitant lessening of the danger of inadvertent or accidental movement or partial dislodgment of the tube from the stomach during stylet removal.

BRIEF DESCRIPTION OF THE DRAWING

The FIGURE is a perspective view of a typical nasogastric tube to which this invention is directed with the stylet partially removed for purposes of illustration.

DETAILED DESCRIPTION OF THE INVENTION

Figure 1:
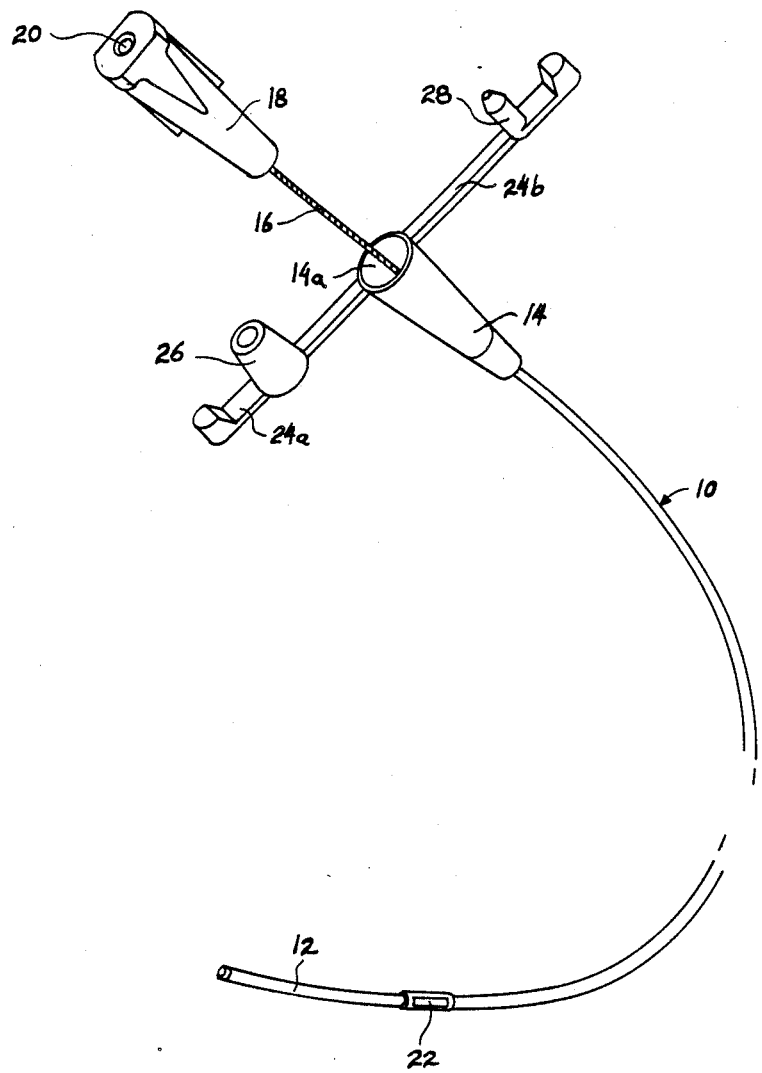

As previously stated, the present invention is directed to reducing the frictional forces encountered in attempting to remove the stylet or stiffening wire from nasogastric tubes following intubation for feeding, aspiration and/or removal of stomach fluids.

Nasogastric devices are of course well known in the medical and surgical arts and a typical device of this description is shown in the illustrative drawing.

As is illustrated therein, nasogastric tube 10, a soft, hollow tubing, has a weighted bolus 12, e.g. a tungsten-weighted bolus, attached to its leading end to help maintain intubation and placement. The opposed or trailing end of tube 10 is secured to hollow cone-shaped tube connector 14. A braided stiffening wire 16 extends from the leading end of tube 10 to where the wire is secured at its trailing end to stylet connector 18 adapted to be removably seated within opening 14a of the tube connector. The top or trailing end of stylet connector 18 has a flushing port 20 adapted for applying water to lubricate the stylet, as will be described more fully hereinafter.

At the leading end of tube 10 a pair of opposed openings in the tube wall or "feeding ports" are provided, one of which, 22, is shown in the drawing.

A pair of "ears" or extending flexible bars 24a and 24b extend on either side of tube connector 14. Ear 24a has a hollow cone-shaped member 26 adapted to be removably seated within opening 14a, by flexing ear 24a, once the stylet and stylet connector are removed. Ear 24b has a solid plug 28 adapted to be inserted in the opening in member 26 when the tube is not in use for fluid transmittal.

In operation, just prior to insertion, the stylet is lubricated by flushing the tube through port 20 with water, e.g. 10–15 cc's of water. The bolus tip is then coated with a surgical lubricant, e.g. a lubricating jelly containing phenyl mercuric borate. The tube is then gently inserted into the nostril, aiming down and back toward the ear.

As the bolus drops off back of the soft palate into the pharynx, the patient is encouraged to swallow, if possible. Giving the patient small amounts of water to sip through a straw is sometimes helpful, if not contraindicated.

The practitioner then continues to gently assist the tube passage down the esophagus and into the stomach until the desired position is reached. In doing so, caution must be exercised not to use force. One must proceed slowly and carefully. Slight gagging is normal. However, if the patient coughs or cannot vocalize or shows signs of respiratory distress, this may indicate that the tube has instead entered the trachea. If this occurs, the tube must be withdrawn and inserted into the esophagus.

Before withdrawing the wire stylet, assurance that the tube has reached the desired position is obtained by one or all of the following methods: (a) auscultation, e.g. by injecting with a syringe 10–20 cc of air through tube/stylet assembly and listening for a bubbling sound in the upper left abdominal quadrant; (b) aspiration by using a syringe to withdraw a small amount of gastric contents; or (c) X-ray.

When the tube is properly positioned, slowly and carefully withdraw the stylet from the tube. If resistance is felt, flush the lumen again with water (as described above) and the stylet is then twisted before attempting further withdrawal. [If resistance is still felt, the nurse or other medical assistant is then instructed to stop and consult a physician, thus confirming and reinforcing the previous discussion with respect to the inadequacy of prior stylet lubricating procedures.]

After the stylet is removed, the tube may be closed off with members 26,28, if desired. The tube is then taped to the patient's nose to stabilize. It is preferably also anchored to the cheek or forehead, avoiding distortion of, or pressure on, the nares.

In accordance with this invention, improved lubriciousness of the stylet and, in turn, materially increased resistance to frictional forces is obtained by coating the stylet with a substantially homogeneous composition consisting essentially of an alkaline earth metal salt of an unsaturated higher fatty acid having at least 16 carbon atoms and as much as equal parts by weight of an alkaline earth metal salt of a saturated higher fatty acid having at least 16 carbon atoms.

Because of cost and availability, the unsaturated acid salt should be either mono- or di-unsaturated. For the same reason, the salts of oleic or linoleic acid are preferred. Preferably, the alkaline earth metal salt will be sodium or potassium, e.g. sodium or potassium oleate or linoleate.

In like manner, the salts of stearic or palmitic acid are preferred for the saturated fatty acid salt component of the lubricity-providing coating.

In the coating compositions of this invention, the effective ingredient for providing the desired lubricity is the unsaturated fatty acid soap, e.g. sodium oleate. However, since these unsaturated soaps are soft, flaky solids in pure form, they cannot be used alone as the coating material. Accordingly, another component is needed as a vehicle for and/or modifier of the properties of the unsaturated soap in order to provide a proper coating on the stylet surface.

In theory, various per se known compatible vehicles could conceivably be employed for coating this soap, e.g. polyvinyl alcohol, gelatin, cellulose esters such as carboxymethyl cellulose, and other such commonly used materials. However, when such vehicles are utilized, the soap tends to wash off quickly upon application of water through the flushing port and accordingly the requisite lubricious coating is not obtained.

Accordingly, a critical aspect of the present invention is the discovery that using up to equal parts by weight of a saturated higher fatty acid salt in combination with the lubricity-providing unsaturated fatty acid soap modifies the coating composition so as to provide the appropriate properties for the contemplated usage of assisting removal of the stylet following intubation. Specifically, in addition to being compatible with the soap so as to form a substantially homogeneous mixture, the saturated fatty acid salt increases the cohesive strength of the coating composition and raises its melting point, thus making it harder.

While, as mentioned previously, up to equal parts by weight of the saturated fatty acid soap may be employed, i.e. 1:1 by weight mixture of the two salts, in the preferred embodiments, the ratio by weight of the unsaturated soap to the saturated salt will be no less than about 4:1. In general, in the preferred embodiments, the coating composition will consist essentially of from about 80 to about 90% by weight of the unsaturated soap, the remainder being the saturated fatty acid salt.

The coating composition may be applied to the stylet from an organic solution by spraying, flowing, immersing or other per se known coating techniques. The preferred solvents for this purpose are ethanol and methanol.

The following examples show by way of illustration and not by way of limitation the practice of this invention.

EXAMPLE 1

Two grams of stearic acid were dissolved in eight grams of oleic acid and the resulting mixture was then dissolved in two volumes of ethanol. Phenolphthalein pH indicator was added in order to visualize the end point of neutral pH. Four molar sodium hydroxide was then added at 50°–55° C. with stirring until the end point was reached. The solution was now pink and very slightly alkaline. The stylet wire from a nasogastric intubation device as shown in the drawing was immersed in the resulting alcoholic solution while maintaining the temperature of around 50°–55° C. The wire was then removed and air dried. The resulting coated wire and tube were then assembled to provide a nasogastric intubation device as shown in the drawing and previously described.

EXAMPLE 2

Example 1 was repeated, except that one gram of stearic acid and nine grams of oleic acid were dissolved in methanol.

In both of the above examples, the coating on the stylet was appreciably harder than the coating obtainable with the oleate alone. The coatings did not flake or rub off when the stylet was inserted in the tube, as was the case with the oleate alone.

The nasogastric tube as prepared above may be employed in the manner heretofore described. In other words, prior to insertion, the device will be flushed with a small quantity of water, as previously described, to provide in effect a soap solution lubricating the wire surface in order to provide a substantial decrease in friction and, in turn, permit easy removal of the wire after intubation is completed.

It will of course be appreciated that the bolus should also be lubricated prior to insertion, which lubrication may be accomplished with the aid of a surgical lubricant, as previously described. Preferably, however, lubrication of the bolus is accomplished by providing a lubricious precursor consisting essentially of a substantially uniform mixture of an unsaturated higher fatty acid containing at least sixteen carbon atoms and a polymer such as polyurethane which is compatible therewith, in accordance with the invention described and claimed in our concurrently filed patent application, Ser. No. (P.F. 1059). As is described therein, when the bolus provided with the above composition is contacted with an aqueous alkaline medium, the surface of the bolus is rendered lubricious. When the present invention is used in conjunction with the invention described and claimed in the aforementioned copending application, it will be appreciated that in lieu of utilizing water at a neutral pH in the flushing port, a slightly alkaline aqueous solution, e.g. on the order of pH 8.5–9 will be utilized in order to convert the acid in the bolus to its soap and thereby lubricate both the wire and bolus in a single step.

To confirm the efficacy of this invention, comparative tests were run to establish the removal force for (1) a dry uncoated stylet wire; (2) a wet uncoated stylet wire; (3) a dry stylet wire coated as in Example 2; and (4) a stylet wire coated as in Example 2 and which has been wetted with water. In these tests, an approximately 7 cm unsupported loop was made in the stylet-containing tube in order to provide some friction simulating actual removal conditions. With both the dry uncoated wire (1) and the wet uncoated wire (2), the wire could not be removed. With the dry wire coated in accordance with this invention (3) 50 grams of force was required for removal. However, when the coated wire was wetted (4) only 37 grams of force was needed, thus confirming the ability of the present invention to solve the task of the invention in a simple an elegant manner, namely to provide a lubricious coating on the stylet which materially improves the surface lubricity so as to facilitate markedly the removal of the wire from the tube following intubation.

Since certain changes may be made without departing from the scope of the invention herein involved, it is intended that all matter described in the foregoing specification and drawing shall be interpreted as illustrative and not in a limiting sense.

What is claimed is:

1. A flexible stylet adapted for being removably inserted within a nasogastric tube in order to assist in intubation, said stylet having a surface coating of a substantially homogeneous non-aqueous mixture consisting essentially of an alkaline earth metal salt of an unsaturated higher fatty acid having at least sixteen carbon atoms; and up to equal parts by weight of an alkaline earth metal salt of a saturated fatty acid having at least sixteen carbon atoms.

2. A stylet as defined in claim 1 wherein said unsaturated fatty acid is oleic or linoleic acid.

3. A stylet as defined in claim 2 wherein said saturated fatty acid is stearic or palmitic acid.

4. A stylet as defined in claim 3 wherein the ratio by weight of said unsaturated fatty acid salt to said saturated fatty acid salt is no less than about 4:1.

5. A stylet as defined in claim 1 wherein said mixture contains from about 80 to about 90 per cent by weight of said unsaturated fatty acid salt.

6. A nasogastric intubation device including a tube adapted to be inserted through the nose and into the stomach, said tube having a leading end for positioning in the stomach and a trailing end, said tube having at least one port adjacent its leading end for passage of fluid to or from said tube; and a flexible stylet removably insertable into said trailing end of said tube to assist in intubation, said stylet having a surface coating of a substantially homogeneous non-aqueous mixture of an alkaline earth metal salt of an unsaturated higher fatty acid having at least sixteen carbon atoms; and up to equal parts by weight of an alkaline earth metal salt of a saturated fatty acid having at least sixteen carbon atoms.

7. A device as defined in claim 6 wherein said unsaturated fatty acid is oleic or linoleic acid.

8. A device as defined in claim 7 wherein said saturated fatty acid is stearic or palmitic acid.

9. A device as defined in claim 8 wherein the ratio by weight of said unsaturated fatty acid salt to said saturated fatty acid salt is no less than about 4:1.

10. A device as defined in claim 6 wherein said mixture contains from about 80 to about 90 per cent by weight of said unsaturated fatty acid salt.

* * * * *